US008953738B2

(12) United States Patent
Tsuchimoto et al.

(10) Patent No.: US 8,953,738 B2
(45) Date of Patent: Feb. 10, 2015

(54) METHOD AND APPARATUS FOR INSPECTING HONEYCOMB STRUCTURE

(75) Inventors: Kazuya Tsuchimoto, Niihama (JP); Teruo Komori, Niihama (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 160 days.

(21) Appl. No.: 13/825,700

(22) PCT Filed: Sep. 22, 2011

(86) PCT No.: PCT/JP2011/071719
§ 371 (c)(1),
(2), (4) Date: Mar. 22, 2013

(87) PCT Pub. No.: WO2012/039480
PCT Pub. Date: Mar. 29, 2012

(65) Prior Publication Data
US 2013/0188769 A1 Jul. 25, 2013

(30) Foreign Application Priority Data
Sep. 24, 2010 (JP) ................................. 2010-213752

(51) Int. Cl.
*G01N 23/00* (2006.01)
*G01N 23/04* (2006.01)
(52) U.S. Cl.
CPC ........ *G01N 23/046* (2013.01); *G01N 2223/646* (2013.01)
USPC ........................................................... 378/4
(58) Field of Classification Search
USPC ....................... 378/4, 19, 62, 98.12
See application file for complete search history.

(56) References Cited

U.S. PATENT DOCUMENTS

| 3,351,760 | A  | * | 11/1967 | Brown ........................ 250/303 |
| 6,154,522 | A  | * | 11/2000 | Cumings ..................... 378/206 |
| 6,341,153 | B1 | * | 1/2002  | Rivera et al. .................... 378/4 |
| 6,637,266 | B1 | * | 10/2003 | Froom ........................... 73/583 |
| 7,336,765 | B1 | * | 2/2008  | Amiton et al. ............. 378/98.12 |
| 2007/0266790 | A1 | * | 11/2007 | Gunasekaran et al. ......... 73/624 |

FOREIGN PATENT DOCUMENTS

| JP | 2001-201465 A | 7/2001 |
| JP | 2004-261644 A | 9/2004 |
| JP | 2004-264644 A | 9/2004 |
| JP | 2005-283547 A | 10/2005 |
| JP | 2007-010492 A | 1/2007 |
| JP | 2008-058116 A | 3/2008 |
| JP | 2008-145308 A | 6/2008 |
| JP | 2010-138770 A | 6/2010 |

OTHER PUBLICATIONS

International Preliminary Report on Patentability and Written Opinion issued Apr. 25, 2013 in International Application No. PCT/JP2011/071719 to Sumitomo Chemical Co., Ltd., et al.

* cited by examiner

*Primary Examiner* — Irakli Kiknadze
(74) *Attorney, Agent, or Firm* — Sughrue Mion, PLLC

(57) ABSTRACT

Obtaining computer-tomography images of a first section at a distance Z1 from one end surface 112d of a honeycomb structure 100 and a second section at a distance Z2 larger than the distance Z1 from the end surface 112d of the honeycomb structure, determining the existence/nonexistence of a plugging portion 114 in at least one of the plurality of passages based on the computer-tomography image of the first section, determining the existence/nonexistence of the plugging portion in the at least one passage based on the computer-tomography image of the second section, and determining the length of the plugging portion based on the result of determination of the existence/nonexistence of the plugging portion based on the computer-tomography image of the first section and the result of determination of the existence/nonexistence of the plugging portion based on the computer-tomography image of the second section.

6 Claims, 4 Drawing Sheets

Z=Z1

Z=Z2

METHOD AND APPARATUS FOR INSPECTING HONEYCOMB STRUCTURE

CROSS REFERENCE TO RELATED APPLICATIONS

This application is a National Stage of International Application No. PCT/JP2011/071719, filed on Sep. 22, 2011, and claims priority from Japanese Patent Application No. 2010-213752 filed Sep. 24, 2010, the contents of which are incorporated herein by reference in their entirety.

TECHNICAL FIELD

The present invention relates to a method and apparatus for inspecting a honeycomb structure.

BACKGROUND ART

As a method of inspecting the length of a plugging portion in a honeycomb structure, a method of inserting an inspection rod is conventionally known (see, for example, Patent Literatures 1 and 2).

CITATION LIST

Patent Literature

Patent Literature 1: Japanese Patent Application Laid-Open Publication No. 2007-10492
Patent Literature 2: Japanese Patent Application Laid-Open Publication No. 2008-58116

SUMMARY OF INVENTION

Technical Problem

The conventional method, however, has the problem that the operation is complicated and time-consuming.

The present invention has been achieved in consideration of the above-described problem and an object of the present invention is to provide a method and apparatus for inspecting a honeycomb structure using a simple operation and capable of inspecting the length of a plugging portion in a short time.

Solution to Problem

According to an aspect of the present invention, there is provided a method of inspecting a honeycomb structure having a partition wall portion forming a plurality of passages opened in opposite end surfaces, and plugging portions closing any one end of each passage, the method including:

a step of obtaining computer-tomography images of a first section at a distance $Z1$ from one end surface of the honeycomb structure and a second section at a distance $Z2$ larger than the distance $Z1$ from the end surface of the honeycomb structure;

a step of determining the existence/nonexistence of the plugging portion in at least one of the plurality of passages based on the computer-tomography image of the first section;

a step of determining the existence/nonexistence of the plugging portion in the at least one passage based on the computer-tomography image of the second section; and a step of determining the length of the plugging portion based on the result of determination of the existence/nonexistence of the plugging portion based on the computer-tomography image of the first section and the result of determination of the existence/nonexistence of the plugging portion based on the computer-tomography image of the second section.

According to an aspect of the present invention, there is provided an apparatus for inspecting a honeycomb structure including:

image obtaining means capable of obtaining a computer-tomography image of any section of the honeycomb structure having partition wall portions forming a plurality of passages opened in opposite end surfaces, and plugging portions closing any one end of each passage;

a command section that makes the image obtaining means obtain computer-tomography images of a first section at a distance $Z1$ from one end surface of the honeycomb structure and computer-tomography images of a second section at a distance $Z2$ larger than the distance $Z1$ from the end surface of the honeycomb structure;

an existence/nonexistence determination section that determines the existence/nonexistence of the plugging portion in at least one of the plurality of passages based on the computer-tomography image of the first section, and determines the existence/nonexistence of the plugging portion in the at least one passage based on the computer-tomography image of the second section; and a plugging length determination section that determines the length of the plugging portion based on the result of determination of the existence/nonexistence of the plugging portion based on the computer-tomography image of the first section and the result of determination of the existence/nonexistence of the plugging portion based on the computer-tomography image of the second section.

According to these method and apparatus, with respect to the passage to be inspected, if the plugging portion exists in the first section and does not exist in the second section, it can be understood that the length of the plugging portion in the passage is larger than $Z1$ and smaller than $Z2$. Also, if the plugging portion exists in the second section, it can be understood that the length of the plugging portion in the passage is larger than $Z2$. Further, if the plugging portion does not exist in the first section, it can be understood that the length of the plugging portion in the passage is smaller than $Z1$. Thus, determination as to whether the length of the plugging portion in the honeycomb structure is larger than the particular value $Z1$ and smaller than the particular value $Z2$ can be easily made.

In the step of determining the length of the plugging portion, it may be determined, with respect to the at least one passage, that the length of the plugging portion in the at least one passage is proper, if the plugging portion exists in the first section and the plugging portion does not exist in the second section, and it may be determined, with respect to the at least one passage, that the length of the plugging portion in the at least one passage is improper, if the plugging portion exists in the second section, or if the plugging portion does not exist in the first section.

The plugging length determination section may determine, with respect to the at least one passage, that the length of the plugging portion in the at least one passage is proper, if the plugging portion exists in the first section and the plugging portion does not exist in the second section, and may determine, with respect to the at least one passage, that the length of the plugging portion in the at least one passage is improper, if the plugging portion exists in the second section, or if the plugging portion does not exist in the first section.

The honeycomb structure may be a fired ceramic body or an unfired ceramic body.

The computer-tomography image may be obtained based on the rate of absorption of electromagnetic waves in the honeycomb structure.

Advantageous Effects of Invention

According to the present invention, a method and apparatus for inspecting a honeycomb structure using a simple operation and capable of inspecting the length of a plugging portion in a short time are provided.

DESCRIPTION OF EMBODIMENTS

An embodiment of the present invention will be described with reference to the drawings. A honeycomb structure 100 to be inspected in the present invention will first be described with reference to FIGS. 1 and 2. The honeycomb structure 100 can be used, for example, as a diesel particulate filter.

Figure 1:
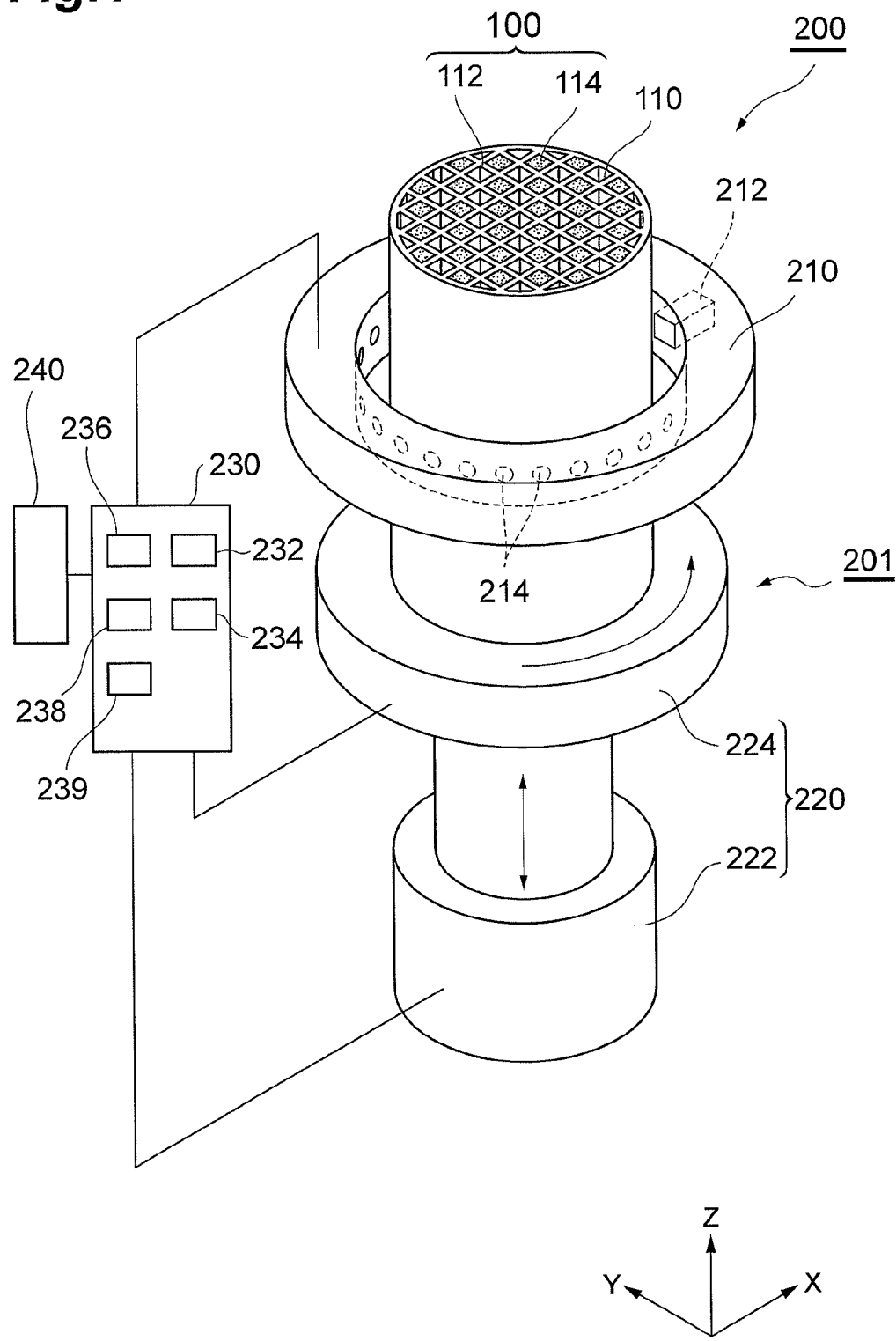
FIG. 1 is a diagrammatic schematic view showing an inspection apparatus according to an embodiment of the present invention.
Figure 2:
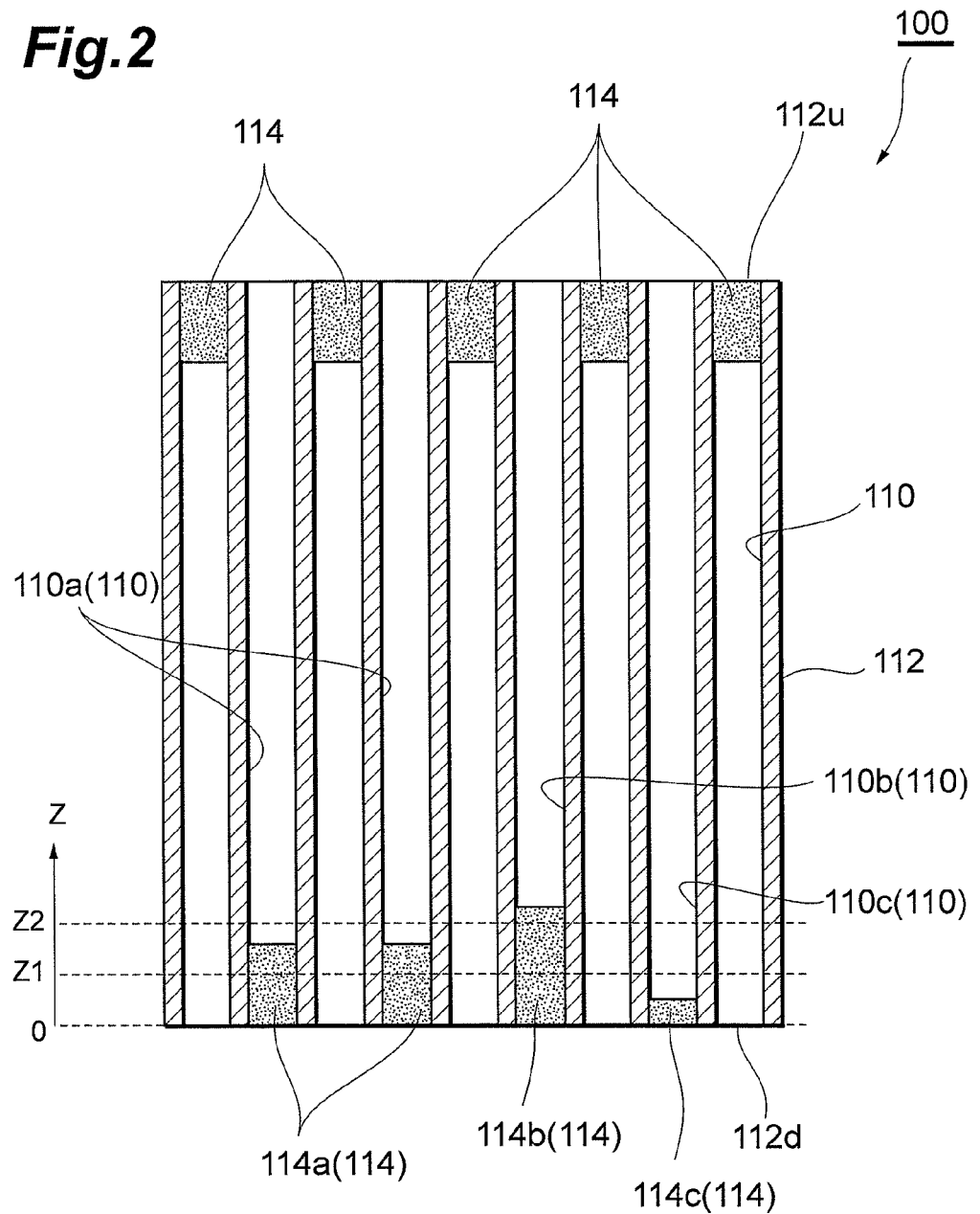
FIG. 2 is a sectional view of parallel to the Z-axis of a honeycomb structure 100 shown in FIG. 1.

The honeycomb structure 100 to be inspected according to the present embodiment is a cylindrical body having, as shown in FIGS. 1 and 2, a partition wall portion 112 forming a plurality of passages 110 extending parallel to each other and open in opposite end surfaces $112u$ and $112d$, and a plurality of plugging portions 114 closing any one end (the upper end or the lower end of FIG. 2) of each passage 110.

The length of each passage 110 in the honeycomb structure 100 extending in the Z-direction is not particularly specified restrictively. The length of each passage 110, however, can be set to 30 to 500 mm, for example. Also, the outside diameter of the honeycomb structure 100 is not particularly specified restrictively. The outside diameter of the honeycomb structure 100, however, can be set to 30 to 500 mm, for example. The sectional shape of each passage 110 is square. The passages 110 are disposed in a square array, i.e., in such a manner that centers of the passage 110 are positioned at the vertices of squares, and that their opposed sides are parallel to each other. The size of the cross section of each passage 110 in terms of the length of each side may be set to 0.5 to 2.5 mm. The thickness of the partition wall portion 112 between the passages 110 may be set to 0.05 to 0.5 mm.

The material of the partition wall portions 112 in the honeycomb structure 100 is a fired porous ceramic (fired body) or a green (unfired ceramic body) before firing of the ceramic. The ceramic is not particularly specified restrictively. Examples of the ceramic, however, include oxides such as alumina, silica, mullite, cordierite, glass and aluminum titanate, silicon carbide, silicon nitride and metals. Further, aluminum titanate may include magnesium and/or silicon.

As described above, one end of each passage 110 in the honeycomb structure 100 is closed by the plugging portion 114. Examples of the material of the plugging portions 114 include the same porous ceramic as that of the honeycomb structure 100, a nonporous ceramic or an unfired body for the ceramic. Preferably, as shown in FIG. 1, the plugging portions 114 are provided in staggered positions alternately selected along each of the row and column directions in the plurality of passages 110 arrayed in matrix form, as seen from each end surface side.

The honeycomb structure 100 thus constructed can be manufactured, for example, in a way described below.

An inorganic compound raw material powder, an organic binder, a solvent and an additive to be added according to need are first prepared. These materials are mixed by a kneading machine or the like to obtain a raw material mixture. The obtained raw material mixture is extruded from an extruder having an outlet opening corresponding to the shape of the partition wall portion, cut by a desired length, and dried by a well-known method, thereby obtaining a green honeycomb molded body. End portions of passages in the green honeycomb molded body are closed with a plugging material by a well-known method to complete an unfired body for the honeycomb structure. This unfired body is fired to complete a fired body for the honeycomb structure. A material body obtained by firing the green honeycomb molded body and by closing the end portions of the passages with a plugging material may be inspected.

An inspection apparatus 200 for inspecting the length of the plugging portions 114 in the honeycomb structure 100 will next be described with reference to FIG. 1.

The inspection apparatus 200 has, as its main components, a probe part 210 that applies a beam to the honeycomb structure 100 from one side and obtains the intensity of the beam that has passed through the honeycomb structure 100, a moving part 220 that holds and moves the honeycomb structure 100, and a computer part 230 connected to the probe part 210 and the moving part 220.

The moving part 220 holds the honeycomb structure 100 so that the axis of the honeycomb structure 100 is set along the Z-axis direction, and includes a rotating part 224 that rotates the honeycomb structure 100 about the Z-axis and a lift part 222 that vertically moves the honeycomb structure 100 along the Z-axis direction.

The probe part 210 has a beam generation source 212 that applies a beam to the honeycomb structure 100, and a beam sensor 214 that detects the intensity of the beam that has transmitted or otherwise passed through the honeycomb structure 100. In the present embodiment, the beam generation source 212 generates a beam expanding in planar form in the X-Y plane, and the intensity of the beam that has transmitted, excited or otherwise passed through the honeycomb structure 100 is detected with a plurality of beam sensors 214 disposed on the same plane. Examples of the beam include electromagnetic waves such as X-rays, gamma rays or terahertz waves (e.g., 0.01 to 10 THz), a particle beam such as a proton ray or a neutron ray, a magnetic field or ultrasound.

The computer part 230 has a control section 232 that controls the probe part 210 and the moving part 220, a command section 234 that issues a command about a measurement place to the control section 232, a CT section 236 that obtains a computer-tomography image with respect to the structure of the honeycomb structure 100 based on information obtained by the probe part 210, an existence/nonexistence determination section 238 that determines whether or not each plugging portion exists based on the obtained image, and a plugging length determination section 239 that determines the length of the plugging portion based on the existence/nonexistence of the plugging portion.

The control section 232 controls the relative positions of the probe part 210 and the honeycomb structure 100 through drive of the moving part 220, controls irradiation and detection of the beam by means of the probe part 210, and obtains data necessary for obtaining a computer-tomography image of a desired section of the honeycomb structure.

The CT section 236 obtains a computer-tomography image at each height Z based on data obtained at any height Z by the probe part 210.

The moving part 220, the probe part 210, the control section 232 and the CT section 234 constitute image obtaining means 201 capable of obtaining a computer-tomography image of any section of the honeycomb structure 100. Such an apparatus is ordinarily called as X-ray CT, MRI or PET, for example.

The command section 234 issues a command described below to the control section 232. The command section 234 first issues a command to obtain data necessary for forming a computer-tomography image of a section at a distance Z1 from the lower end surface 112d of the honeycomb structure 100 as shown in FIG. 2. More specifically, the lift part 222 is first driven so that the height of the probe 210 is adjusted to Z1. Subsequently, the step of obtaining intensity data such as the rate of absorption of the beam by driving the probe part 210 and the step of rotating the honeycomb structure 100 about the Z-axis through a small angle by driving the moving part 224 are repeated to obtain data necessary for obtaining a computer-tomography image.

Subsequently, the command section 234 issues a command to the control section 232 to obtain data necessary for forming a computer-tomography image at a section at a distance Z2 from the lower end surface 112d of the honeycomb structure 100. It is assumed that Z1<Z2.

Z1 and Z2 are not particularly specified restrictively. Z1, however, can be set to 1 to 3 mm, for example. Also, Z2 can be set to 3 to 6 mm, for example, and Z2−Z1 can be set to a value larger than 0 and equal to or smaller than 5 mm. In particular, it is preferred that a desired length of the plugging portions is assumed and Z1 and Z2 are set so that one end of the plugging portion having the desired length is located between positions corresponding to Z1 and Z2.

The existence/nonexistence determination section 236 determines whether or not each plugging portion exists in the passages to be inspected based on two computer-tomography images. More specifically, the existence/nonexistence of the plugging portion 114 in at least one of the plurality of passages is first determined based on a computer-tomography image at the height Z1. Also, the existence/nonexistence of the plugging portion 114 in the at least one passage, the same passage as that mentioned above, is determined based on a computer-tomography image at the height Z2. The method of determination as to the existence/nonexistence of the plugging portion 114 is not particularly specified restrictively. A well-known method can be used as the determination method. For example, determination can be made from a light/dark condition in each passage portion in images. Preferably, tomography images are binarized by using a light/dark threshold value that enables existence/nonexistence distinction and determination is made by means of the binarized images.

Preferably, in the present embodiment, the existence/nonexistence of the plugging portion 114 at the height Z1 and at the height Z2 is made with respect to all the passages to have the ports closed, and the determination results are stored. Existence/nonexistence determination may be made through comparison between a normal binarized image pattern and an actual binarized image pattern.

The plugging length determination section 239 determines the length of each plugging portion 114. More specifically, in a case where the plugging portion 114 exists in the computer-tomography image at the height Z1 and the plugging portion 114 does not exist in the computer-tomography image at the height Z2 in the target passage 110, it is determined that the length of the plugging portion in the target passage is proper.

In a case where the plugging portion 114 exists in the computer-tomography image at the height Z2 in the target passage 110, it is determined that the length of the plugging portion 114 in the passage 110 exceeds Z2 and is improper.

Further, in a case where the plugging portion 114 does not exist in the computer-tomography image at the height Z1, it is determined that the length of the plugging portion 114 in the passage 110 is smaller than Z1 and is improper.

In the present embodiment, the length of the plugging portion 114 is a length in the Z-direction along the axis of the passage 110.

This inspection apparatus 200 has a monitor 240 that displays images including tomographic images.

A method of inspection with the inspection apparatus 200 in the present embodiment will next be described. It is assumed here that in the honeycomb structure 100 to be inspected the lengths of the plugging portions 114a of the passages 110a are larger than Z1 and smaller than Z2; the length of the plugging portion 114b of the passage 110b is larger than Z2; and the length of the plugging portion 114c of the passage 110c is smaller than Z1, as shown in the FIG. 2.

Figure 3:
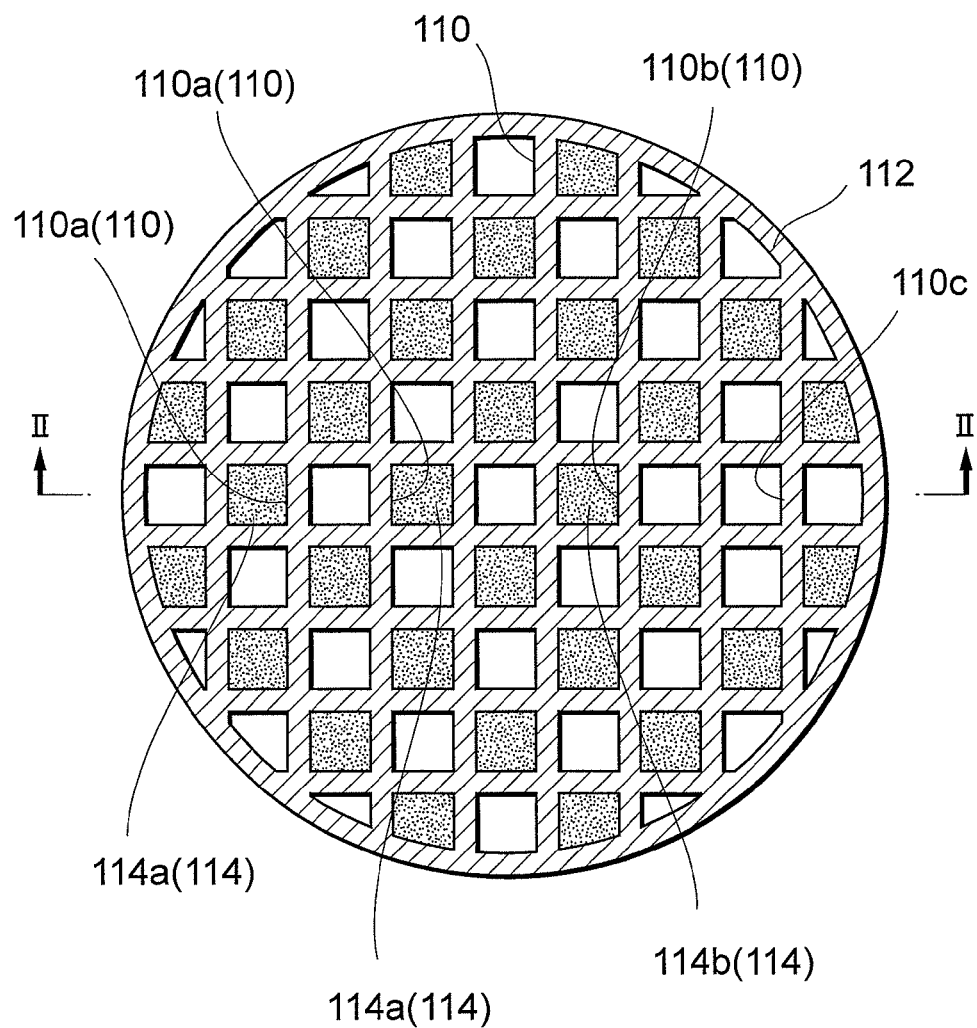
FIG. 3 is a schematic view showing a computer-tomography image at a distance Z1 of the honeycomb structure 100 shown in FIG. 2.

This honeycomb structure 100 is placed on the moving part. At a command from the command section 234, data on beam absorption or the like at the X-Y section (first section) at the distance Z1 from the end surface of the honeycomb structure 100 is obtained and data on beam absorption or the like at the X-Y section (second section) at the distance Z2 from the end surface of the honeycomb structure 100 is also obtained. Subsequently, the CT section 236 obtains computer-tomography images at the distances Z1 and Z2 based on these data items. Schematic views of obtained images are shown in FIGS. 3 and 4.

Subsequently, the existence/nonexistence determination section 238 determines whether the plugging portions exist in the passages. The image shown in FIG. 3 is an image of the section at the height Z=Z1. Solids exist in the passages 110a and 110b. That is, it can be determined that the plugging portions 114a and 114b exist. On the other hand, no solid exists in the passage 110c and it can be determined that the plugging portion 114c does not reach the height Z1.

Figure 4:
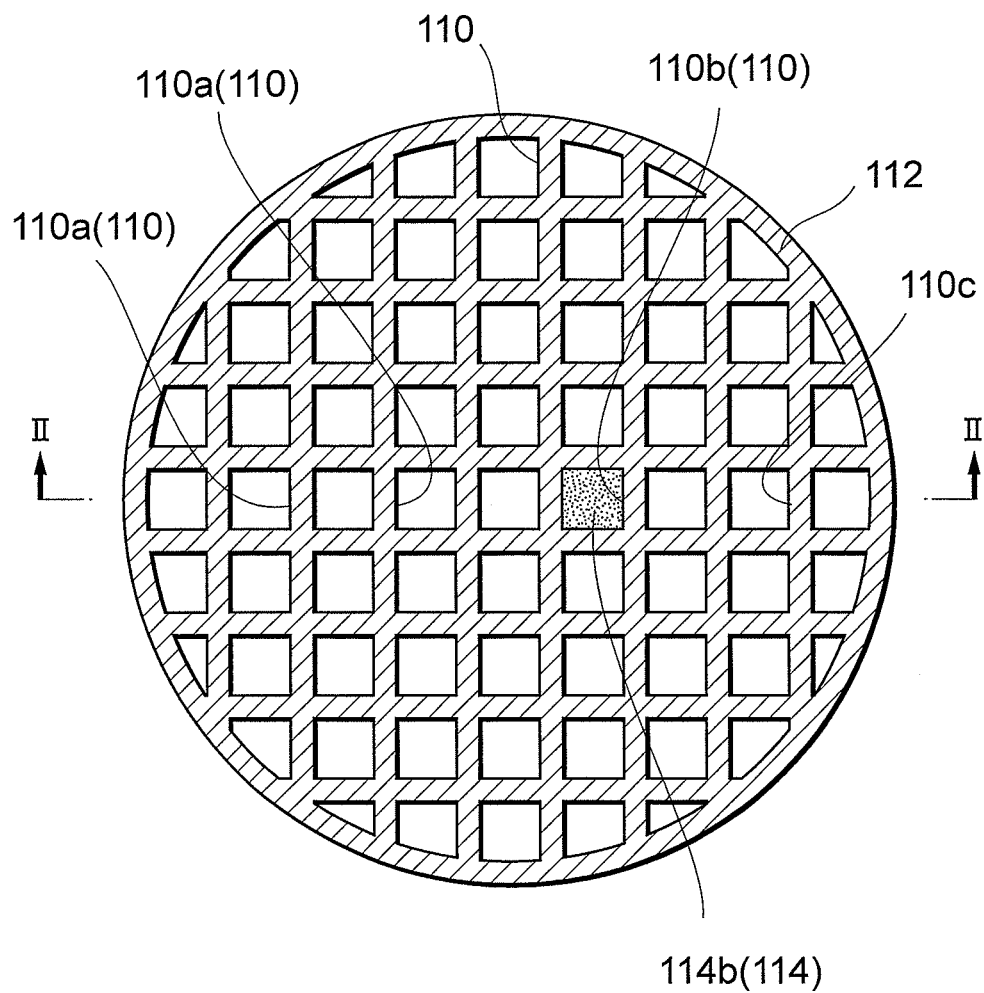
FIG. 4 is a schematic view showing a computer-tomography image at a distance Z2 of the honeycomb structure 100 shown in FIG. 2.

The image shown in FIG. 4 is an image of the section at the height Z=Z2. No solids exist in the passages 110a and 110c and it can be understood that the plugging portions 114a and 114c do not reach the height Z2. On the other hand, a solid exists in the passage 110b and it can be understood that the plugging portion 114c extends beyond the height Z2.

With respect to the passage 110a, the plugging length determination section 239 determines that the length of the plugging portion is larger than Z1 and smaller than Z2 and is proper, since the plugging portion exists in the computer-tomography image at the height Z1, and since the plugging portion does not exist in the computer-tomography image at the height Z2.

On the other hand, the plugging length determination section 239 determines that the length of the plugging portion 114b in the passage 110b is larger than Z2 and is improper, since the plugging portion 114 exists in the computer-tomography image at the height Z2 in the passage 110b.

Further, the plugging length determination section 239 determines that the length of the plugging portion 114c in the passage 110c is smaller than Z1, since the plugging portion 114 does not exist in the computer-tomography image at the height Z1 in the passage 110c.

Inspection of the length of the plugging portion as described above can be performed with respect to each passage in which the plugging portion 140 is to be provided, and can be performed on each of the upper end surface 112*u* and the lower end surface 112*d* of the honeycomb structure 100.

In the present embodiment, determination as to whether the length of the plugging portion in the honeycomb structure 100 is larger than Z1 and smaller than Z2 can be easily made. Since obtaining tomographic images at two heights with respect to each end surface suffices, inspection can be performed in a short time. Moreover, even if a large number of passages exist, determination can be easily made with respect to each passage.

The present invention is not limited to the above-described embodiment. Various modifications can be made in the embodiment.

For example, in the above-described embodiment, while determination as to the existence/nonexistence of the plugging portion and determination as to the length of the plugging portion are made by a computer, these determinations may be made by a human operator upon displaying the images on the monitor 240.

While the passages 110 in the honeycomb structure 100 are vertically disposed in the above-described embodiment, the present invention can also be implemented when the passages 110 are disposed in a different direction, e.g., a horizontal direction.

The construction of the moving part 220 is not particularly specified restrictively. For example, the moving part 220 may move the probe part 210 instead of moving the honeycomb structure 100. The moving part 220 capable of relatively moving the probe part 210 and the honeycomb structure 100 may suffice.

Also, the construction of the probe part 210 is not particularly specified restrictively. The probe part 210 capable of obtaining data necessary for obtaining computer-tomography images may suffice.

In the above-described embodiment, the sectional shape of the passage 110 is not limited to a generally square shape. It can be made rectangular, circular, elliptical, triangular, hexagonal, or octagonal, for example. Passages differing in diameter and sectional shape may be mixedly provided as passages 110. Also, in the arrangement shown in FIG. 1, the passages are disposed in a square array. However, the array of the passages is not limited to the square array. The passages can be disposed in a regular-triangle array, in which the center axes of the passages are disposed at the vertices of regular triangles in a section, a staggered array or the like. Further, the external shape of the honeycomb filter is not limited to the cylinder. For example, it can be a triangular prism, a rectangular prism, a hexagonal prism, an octagonal prism or the like.

In the above-described embodiment, the image of the section at the height Z=Z1 is first obtained and the image at the height Z2 is thereafter obtained. However, these images may be obtained in the reverse order.

REFERENCE SIGNS LIST

100: honeycomb structure, 112*u*, 112*d*: end surface, 110: passage, 112: partition wall portion, 114, 114*a*, 114*b*, 114*c*: plugging portion, 200: inspection apparatus, 236: CT section (command section), 238: existence/nonexistence determination section, 239: plugging length determination section.

The invention claimed is:

1. A method of inspecting a honeycomb structure having a partition wall portion forming a plurality of passages opened in opposite end surfaces, and plugging portions closing any one end of each passage, the method comprising:
    a step of obtaining computer-tomography images of a first section at a distance Z1 from one end surface of the honeycomb structure and a second section at a distance Z2 larger than the distance Z1 from the end surface of the honeycomb structure;
    a step of determining the existence/nonexistence of the plugging portion in at least one of the plurality of passages based on the computer-tomography image of the first section;
    a step of determining the existence/nonexistence of the plugging portion in the at least one passage based on the computer-tomography image of the second section; and
    a step of determining the length of the plugging portion based on the result of determination of the existence/nonexistence of the plugging portion based on the computer-tomography image of the first section and the result of determination of the existence/nonexistence of the plugging portion based on the computer-tomography image of the second section.

2. The method according to claim 1, wherein, in the step of determining the length of the plugging portion, it is determined, with respect to the at least one passage, that the length of the plugging portion in the at least one passage is proper, if the plugging portion exists in the first section and the plugging portion does not exist in the second section, and it is determined, with respect to the at least one passage, that the length of the plugging portion in the at least one passage is improper, if the plugging portion exists in the second section, or if the plugging portion does not exist in the first section.

3. The method according to claim 1, wherein the honeycomb structure is a fired ceramic body or an unfired ceramic body.

4. The method according to claim 1, wherein the computer-tomography image is obtained based on the rate of absorption of electromagnetic waves in the honeycomb structure.

5. An apparatus for inspecting a honeycomb structure comprising:
    image obtaining means capable of obtaining a computer-tomography image of any section of the honeycomb structure having partition wall portions forming a plurality of passages opened in opposite end surfaces, and plugging portions closing any one end of each passage;
    a command section that makes the image obtaining means obtain computer-tomography images of a first section at a distance Z1 from one end surface of the honeycomb structure and computer-tomography images of a second section at a distance Z2 larger than the distance Z1 from the end surface of the honeycomb structure;
    an existence/nonexistence determination section that determines the existence/nonexistence of the plugging portion in at least one of the plurality of passages based on the computer-tomography image of the first section, and determines the existence/nonexistence of the plugging portion in the at least one passage based on the computer-tomography image of the second section; and
    a plugging length determination section that determines the length of the plugging portion based on the result of determination of the existence/nonexistence of the plugging portion based on the computer-tomography image of the first section and the result of determination of the existence/nonexistence of the plugging portion based on the computer-tomography image of the second section.

6. The apparatus according to claim 5, wherein the plugging length determination section determines, with respect to the at least one passage, that the length of the plugging portion in the at least one passage is proper, if the plugging portion exists in the first section and the plugging portion does not exist in the second section, and determines, with respect to the at least one passage, that the length of the plugging portion in the at least one passage is improper, if the plugging portion exists in the second section, or if the plugging portion does not exist in the first section.

* * * * *